United States Patent [19]

Matsumoto et al.

[11] Patent Number: 4,631,147
[45] Date of Patent: Dec. 23, 1986

[54] CYCLOALKAN-1-OL DERIVATIVES AND PERFUME COMPOSITIONS COMPRISING THE SAME

[75] Inventors: Kiyoshi Matsumoto; Yoshiaki Fujikura, both of Utsunomiya; Motoki Nakajima, Miyashitomachi, all of Japan

[73] Assignee: Kao Corporation, Tokyo, Japan

[21] Appl. No.: 826,905

[22] Filed: Feb. 6, 1986

[30] Foreign Application Priority Data

Feb. 18, 1985 [JP] Japan .................. 60-30049
Oct. 14, 1985 [JP] Japan .................. 60-228439

[51] Int. Cl.$^4$ .................. C11B 9/00; C07C 35/20; A61K 7/46
[52] U.S. Cl. .................. 252/522 R; 568/821; 568/822; 568/832; 568/834
[58] Field of Search .............. 568/821, 822, 832, 834; 252/522 R

[56] References Cited

U.S. PATENT DOCUMENTS 4,214,098  7/1980  Jong et al. ................. 568/821
4,307,255  12/1981  Kane ....................... 568/834
4,371,722  2/1983  Kane ....................... 568/834

OTHER PUBLICATIONS

Lomas et al, "Chemical Abstracts", vol. 96(23) p. 198880k.

*Primary Examiner*—Werren B. Lone
*Attorney, Agent, or Firm*—Oblon, Fisher, Spivak, McClelland & Maier

[57] ABSTRACT

Novel cycloalkan-1-ol derivatives having a formula (I):

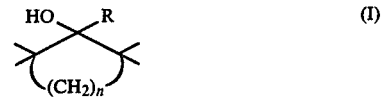

wherein R represents a hydrogen atom, lower alkyl group or an allyl group, and n is an integer of 3 or 4 provided that when n is 3, R is not a hydrogen atom or lower alkyl group, have a woody, green and earthy odor and may be prepared according to one of the following reaction formulae:

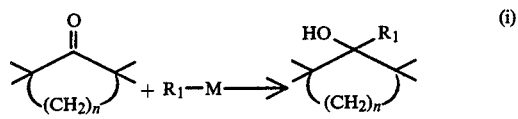

where $R_1$ represents a lower alkyl group or allyl group, M represents MgX or lithium atom, n is a value of 3 or 4, and X represents a halogen atom.

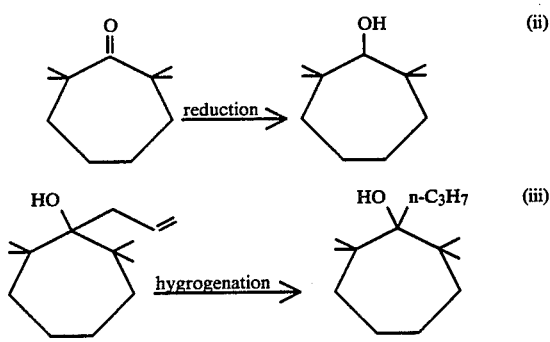

The derivatives (I) may be blended with other perfumes to give perfume compositions and thus obtained compositions can be widely applied to various articles which require aromatizing such as perfumes, soaps, shampoos, hair rinses, cosmetics, hair sprays and the like.

2 Claims, No Drawings

CYCLOALKAN-1-OL DERIVATIVES AND PERFUME COMPOSITIONS COMPRISING THE SAME

BACKGROUND OF THE INVENTION i. Field of the Invention

This invention relates to cycloalkan-1-ol derivatives of the following formula (I)

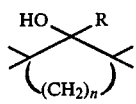
(I)

in which R represents a hydrogen atom, lower alkyl group or allyl group, and n is an integer of 3 or 4 provided that when n is 3, R is not a hydrogen atom or lower alkyl group. The invention also relates to perfume compositions comprising the derivatives.

ii. Description of the Prior Art

A number of saturated or unsaturated alcohols are known to be useful as perfumes [Osamu Okuda, "Bibliology of Perfume Chemistry (II)", Hirokawa Shoten, p. 482–681 (1980)].

For instance, various cyclohexan-1-ols are known including 1-alkyl-2,2,6,6-tetramethylcyclohexan-1-ols of the following formula (II)

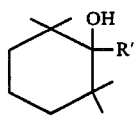
(II)

in which R' represents methyl group, ethyl group, n-propyl group or t-butyl group [J. S. Lomas et al., J. Chem. Soc., 1982, Perkin Trans 2(2), 221 and J. Org. Chem., 1979, 44, 1647], and 1-substituted-2,2,6-trimethylcyclohexan-1-ols of the following formula (III)

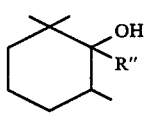
(III)

in which R" represents $C_2H_5$, $CH_2C\equiv CH$, $CH_2CH=CH_2$, $CH_2CH=CHCH_3$, $CH_2CH=C(CH_3)_2$, $C_4H_9$ or $C\equiv CH$ [Bull. Chem. Soc. Jap., 1972, 45, 1147; Bull. Soc. Chim. Fr., 1969, 4023; Helv. Chim. Acta. 1974, 57, 496; "Essential Oils", Allured Publishing Corp., (1981), 267; and DE No. 3003-518]. Of these known compounds, however, fragrant compounds are only 1-substituted-2,2,6-trimethylcyclohexan-1-ols of the formula (III) wherein R" is $C_4H_9$ or $C\equiv CH$, with the odor being sweet floral or minty for the former and woody or earthy for the latter.

Since it is general that the fragrances of compounds completely differ from one another depending on the slight difference in structure, it is very important to prepare a variety of compounds for investigation of the fragrance in order to obtain novel perfumes.

SUMMARY OF THE INVENTION

We have made intensive studies to obtain compounds useful as a perfume and, as a result, found that cycloalkan-1-ol derivatives which are hitherto unknown compounds first prepared by us have an inherent fragrance.

The present invention is accomplished on the basis of the above finding.

Thus, the present invention contemplates to provide novel cycloalkan-1-ol derivatives (I) and perfume compositions comprising the derivatives.

DETAILED DESCRIPTION OF THE INVENTION AND PREFERRED EMBODIMENTS

The cycloalkan-1-ol derivatives (I) of the invention are prepared, for example, by one of the following methods.

Method 1:

According to the following reaction formula, a compound of the formula (V) is reacted with tetramethylcycloalkyl ketone (IV)

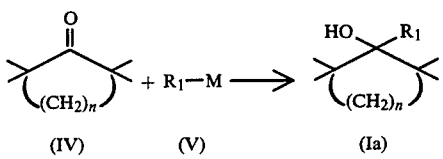

(IV)　　(V)　　(Ia)

in which $R_1$ represents a lower alkyl or allyl group, M represents MgX or lithium atom, n is a value of 3 or 4, and X represents a halogen atom.

The compound of the formula (V) which is one of the starting materials used in this method can be readily prepared by reaction of metallic magnesium or lithium with a lower alkyl halide such as a lower alkyl bromide or lower alkyl chloride or an allyl halide such as allyl bromide or allyl chloride. Accordingly, the reaction for obtaining the compound (Ia) of the invention may be effected by preparing the compound of the formula (V), to which the compound of the formula (IV) is subsequently added. Alternatively, the reaction may be carried out by simultaneously adding the compound of the formula (IV), a lower alkyl halide or allyl halide and metallic magnesium or lithium while permitting the compound of the formula (V) to be produced in the reaction mixture.

The amount of the compound of the formula (V), the lower alkyl halide or ally halide is generally not less than 1 equivalent, preferably not less than 1.2 equivalents, relative to the compound of the formula (IV).

The solvents used for these reactions may be those which are ordinarily used in the reaction between ketones and Grignard reagents or lithium reagents. Preferable examples of such solvents include ethers such as diethyl ether, tetrahydrofuran, diglyme (dimethyl cellosolve) and the like.

The reaction time and temperature depend on the type of solvent and are preferably from 1 to 5 hours and from room temperature to 100° C., respectively.

Method 2:

According to the following formula, 2,2,7,7-tetramethylcycloheptanone is reduced.

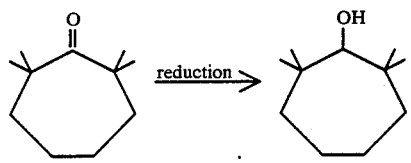

This reduction reaction may be conducted by any methods ordinarily used for the reduction of ketones. Typical methods include a reduction reaction with a metal hydride such as lithium aluminium hydride or sodium borohydride; and a hydrogenation reaction using transition metal catalysts such as platinum oxide, ruthenium/active carbon or Cu-Cr catalysts.

The reduction reaction using a metal hydride can be carried out by an ordinary method described in literature [e.g. L. F. Fieser & M. Fieser, "Reagents for Organic Synthesis" John Wiley & Sons Inc. (1967)].

On the other hand, the hydrogenation reaction using a metal catalyst may be effected in the absence of a solvent or in solvents including, for example, saturated hydrocarbons such as n-hexane, alcohols such as methanol, ethanol and the like and ethers such as diethyl ether, THF, dioxane and the like. The reaction temperature generally ranges from 100° to 250° C., preferably from 150° to 250° C.

Method 3:

According to the following formula, 1-allyl-2,2,7,7-tetramethylcycloheptan-1-ol is hydrogenated in the presence of a metal catalyst.

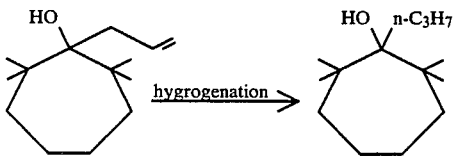

The catalysts used for this hydrogenation reaction may be those which are ordinarily used for the hydrogenation of olefins. Preferable examples of such catalysts include transition metal catalysts such as Raney nickel, palladium/active carbon or platinum oxide. The hydrogenation reaction using a metal catalyst may be effected in the absence of a solvent or in solvents including, for example, saturated hydrocarbons such as n-hexane, aromatic hydrocarbons such as benzene, toluene and the like, alcohols such as methanol, ethanol and the like and ethers such as diethyl ether, THF, dioxane and the like. The reaction temperature generally ranges from room temperature to 250° C., preferably from room temperature to 100° C.

After completion of the reaction, cycloalkan-1-ol derivatives (I) are isolated from the reaction mixture and purified by ordinary procedures including extraction, washing, distillation and the like.

The resultant compound (I) of the invention has a woody, green, earthy or patchouli oil-like odor and may be used as it is. Alternatively, it may be blended with other perfumes to give perfume compositions.

In the preparation of the perfume composition, compound (I) of the invention is added in an amount of 0.1 to 20 wt % (hereinafter referred to simply as %), preferably 0.5 to 5%, though not restrictive.

Perfumes having fougere, woody, animal-like and amber-like odor such as, for example, methyl ionone, oak moss absolute, lavender oil and the like are preferably used in combination.

As described before, the compounds of the invention have a woody, green and earthy odor and particularly such a odor similar to norpatchulenol which is an important fragrance component in patchuli oil, and thus perfume compositions comprising the compounds have the fragrance.

Accordingly, the compounds of the invention are considered to be excellent as a compounding material for various perfumes and can be widely applied to various articles which require aromatizing, e.g. high grade perfume compositions, perfumes, soaps, shampoos, hair rinses, detergents, cosmetics, hair sprays, aromatics and the like. The present invention is described in more detail by way of examples.

EXAMPLE 1

Synthesis of 1-allyl-2,2,6,6-tetramethylcyclohexan-1-ol

Magnesium (11.5 g, 0.48 moles) and dried diethyl ether (300 ml) were added, in this order, to one liter four-necked flask equipped with a mechanical stirrer, a dropping funnel, a thermometer, a reflux condenser and a nitrogen gas inlet tube and stirred at room temperature. While stirring at room temperature, a mixed solution of allyl bromide (57.7 g, 0.48 moles)/dried diethyl ether (100 ml) was dropped to the mixture in 2 hours. The resulting mixture was heated under reflux for 30 minutes. Into the mixture was dropped a mixed solution of 2,2,6,6-tetramethylcyclohexanone (49 g, 0.32 moles)/dried diethyl ether (100 ml) in about 40 minutes while stirring under heating and refluxing conditions. The mixture was further stirred for 2 hours under refluxing conditions. The resultant reaction mixture was poured into iced water, followed by adding a 1N hydrochloric acid aqueous solution to render the mixture weakly acidic and separating it into two layers. The organic layer was washed with a saturated sodium bicarbonate aqueous solution (50 ml) and then with water (50 ml) three times. The organic layer was dried over anhydrous magnesium sulfate and separated by filtration, followed by concentration and fractionation to obtain 42.7 g (yield 68%) of the captioned compound. This compound was a colorless transparent liquid having a woody, green, earthy and patchuli oil-like odor.

Boiling point: 128° C./14 mmHg.

Elementary analysis (for $C_{13}H_{24}O$): Calculated (%): C 79.5, H 12.3. Found (%): C 79.3, H 12.5.

IR analysis (liquid film, $cm^{-1}$): 3600 ($\nu_{OH}$); 3080 [$\nu_{CH}$ (=CH—, =CH$_2$)]; 2950, 2920, 2870 ($\nu_{CH}$); 1635 ($\nu_{C=C}$); 970, 910 [$\delta_{CH}$(out-of-plane deformation vibration of —CH=CH$_2$)].

$^1$H-NMR (CDCl$_3$ solvent, TMS internal standard, $\delta$): 6.37–5.67 (—CH$_2$—C$\underline{H}$=CH$_2$, 1H, m); 5.18–4.85 (—CH$_2$—CH=C$\underline{H}_2$, 2H, m); 2.45 (—C$\underline{H}_2$—CH=CH$_2$, 2H, d, J=8.0 Hz); 2.10–1.20 [—(C$\underline{H}_2$)$_3$—and —O$\underline{H}$, 7H, m]; 1.10 and 0.98 (—C$\underline{H}_3$, 12H, s).

—C-NMR [CDCl$_3$ solvent, TMS internal standard, $\delta_c$, (multiplet, relative intensity)]: 18.9(t,1), 25.0(q,2), 28.8(q,2), 36.5(t,1), 37.8(t,2), 39.8(t,1), 77.3(s,0.2), 117.5(t,1), 136.9(d,1).

MS (relative intensity):

The results of a gas mass measurement using a capillary column [methyl silicone made by Hullet Paccard Co., Ltd., with a column length of 25 m]196(M+, 12), 155(45), 137(62), 112(79), 111(63), 109(68), 97(73), 82(83), 70(71), 69(100).

EXAMPLE 2

Synthesis of 1-allyl-2,2,7,7-tetramethylcycloheptan-1-ol (i) 2,2,7,7-Tetramethylcycloheptanone Sodium amide (39.01 g, 1.0 mole) and toluene (400 ml) were added, in this order, to one liter four-necked flask equipped with a mechanical stirrer, a dropping funnel, a thermometer, a reflux condenser and a nitrogen gas inlet tube, followed by heating under reflux in an atmosphere of nitrogen. A mixed solution of diisopropyl ketone (45.68 g, 0.4 moles)/1,4-dichlorobutane (50.80 g, 0.4 moles) was added to the mixture in 3.5 hours while stirring under refluxing conditions. The resulting mixture was stirred for 5 hours under heating and refluxing conditions. After cooling, water (200 ml) was added to the reaction mixture for separation into two layers. The resulting organic layer was neutralized and washed with a 10% sulfuric acid aqueous solution (50 ml), followed by washing with a 10% sodium carbonate aqueous solution (50 ml) and then twice with a saturated saline solution (100 ml). The organic layer was dried over anhydrous magnesium sulfate and separated by filtration, followed by concentration and fractionation to obtain 34.43 g (yield 51.2%) of the captioned compound.

Boiling point: 98° C./20 mmHg. Elementary analysis (for $C_{11}H_{20}O$): Calculated (%): C 78.51, H 11.98. Found (%): C 78.32, H 11.89.

IR analysis (liquid film, cm$^{-1}$): 2960, 2920, 2860 ($\nu_{CH}$), 1690 ($\nu_{C=O}$).

$^1$H-NMR (CDCl$_3$ solvent, TMS internal standard, δ): 1.60 (—CH$_2$—, 8H, s). 1.16 (—CH$_3$, 12H, s).

MS (relative intensity): The results of a gas mass measurement using the same capillary column as used in Example 1 are shown below. 168(M$^+$, 24), 83(19), 81(24), 70(22), 69(92), 57(31), 56(100), 55(35), 43(20), 41(43).

(ii) 1-Allyl-2,2,7,7-tetramethylcycloheptan-1-ol

Magnesium (5.37 g, 0.221 moles) was added to 500 ml four-necked flask equipped with a mechanical stirrer, a dropping funnel, a thermometer, a reflux condenser and a nitrogen gas inlet tube, into which nitrogen gas was passed to remove moisture from the flask. Thereafter, a small amount of a mixed solution of ally bromide (1.5 g, 0.0124 moles)/dried diethyl ether (7.5 ml) was dropped while stirring, followed by dropping a mixed solution of allyl bromide (21.29 g, 0.176 moles)/2,2,7,7-tetramethylcycloheptanone (24.68 g, 0.147 moles)/dried diethyl ether (75 ml) in 2 hours while cooling to 15° C. or below on an iced water bath. The resulting mixture was stirred for 1 hour while keeping at 15° C. or below. Thereafter, the reaction mixture was treated in the same manner as in Example 1, thereby obtaining 23.03 g (yield 74.5%) of the captioned compound. This compound was a colorless transparent liquid having a woody, green, earthy and patchuli oil-like odor.

Boiling point: 115° C./5 mmHg.

Elementary analysis (for $C_{14}H_{26}O$): Calculated (%): C 79.94, H 12.46. Found (%): C 79.75, H 12.63.

IR analysis (liquid film, cm$^{-1}$): 3580 ($\nu_{OH}$); 3080 [$\nu_{CH}$ (=CH—, =CH$_2$)]; 2950, 2920, 2870 ($\nu_{CH}$); 1635 ($\nu_{C=C}$); 980, 920 [$\delta_{CH}$ (out-of-plane deformation vibration of —CH=CH$_2$)].

$^1$H-NMR (CDCl$_3$ solvent, TMS internal standard, δ): 6.31–5.61 (—CH$_2$—CH=CH$_2$, 1H, m); 5.15–4.88 (—CH$_2$—CH=CH$_2$, 2H, m); 2.43 (—CH$_2$—CH=CH$_2$, 2H, d, J=8.0 Hz); 2.02–1.20 [—(CH$_2$)$_4$— and —OH, 9H, m]; 1.05 and 0.98 (—CH$_3$, 12H, s).

MS (relative intensity): The results of a gas mass measurement using the same capillary column as used in Example 1 are shown below. 210(M$^+$, 4), 111(64), 95(78), 82(63), 81(89), 71(64), 69(99), 55(79), 43(100), 41(83).

EXAMPLE 3

Synthesis of 2,2,7,7-tetramethylcycloheptan-1-ol

Lithium aluminium hydride (3.80 g, 0.1 mole) and dried diethyl ether (100 ml) were added to a one liter four-necked flask equipped with a mechanical stirrer, a dropping funnel, a thermometer, a reflux condenser and a calcium chloride tube and stirred at room temperature. A mixed solution of 2,2,7,7-tetramethylcycloheptanone (33.66 g, 0.2 moles)/dried diethyl ether (60 ml) was dropped into the mixture in 1 hour while stirring at room temperature. The mixture was stirred at room temperature for 1 hour. Subsequently, water (40 ml) and a 10% sulfuric acid aqueous solution (250 ml) were added in this order to the resulting reaction mixture to separate it into two layers. The resulting organic layer was washed twice with saturated saline solution (100 ml). The organic layer was dried over anhydrous magnesium sulfate and separated by filtration, followed by concentration and fractionation to obtain 33.45 g (yield 98.2%) of the captioned compound. This compound was a white solid having a woody, earthy, camphoraceous and hay-like odor.

Boiling point: 105° C./16 mmHg.

Melting point (in sealed tube): 47.7° to 48.6° C.

Elementary analysis (for $C_{11}H_{22}O$): Calculated (%): C 77.58, H 13.02. Found (%): C 77.32, H 12.92.

IR analysis (thin film, cm$^{-1}$): 3460 ($\nu_{OH}$); 2950, 2920, 2860 ($\nu_{CH}$).

$^1$H-NMR (CDCl$_3$ solvent, TMS internal standard, δ): 3.02 (CH—OH, 1H, d, J=6.0 Hz); 1.70 (>CH—OH, 1H, d, J=6.0 Hz); 1.47 [—(CH$_2$)$_4$—, 8H, s]; 1.00 and 0.97 (—CH$_3$, 12H, s).

MS (relative intensity): The results of a gas mass measurement using the same capillary column as used in Example 1 are shown below. 170(M$^+$, 4), 109(25), 96(24), 85(27), 82(100), 81(20), 69(21), 55(21), 43(20), 41(18).

EXAMPLE 4

Synthesis of 1,2,2,7,7-pentamethylcycloheptan-1-ol:

A mixed solution of methyl iodide (23.90 g, 0.16 moles)/dried diethyl ether (10 ml) was dropped into a mixture of magnesium (2.90 g, 0.12 moles)/dried diethyl ether (20 ml) in 1 hour while stirring under water-cooling conditions. The mixture was stirred for 48 hours at room temperature and subjected to separation by filtration. Into the resulting filtrate was dropped a mixed solution of 2,2,7,7-tetramethylcycloheptanone (16.80 g, 0.10 mole)/dried diethyl ether (30 ml) in 30 minutes while stirring at room temperature. The mixture was stirred at room temperature for 48 hours. The resulting reaction mixture was treated in the same manner as in Example 1 to obtain 10.20 g (yield 55.3%) of the captioned compound. This compound was a white solid having a woody, earthy camphoraceous and patchuli oil-like odor.

Boiling point: 102° C./10 mmHg.

Melting point (in sealed tube): 82.7° C.

Elementary analysis (for $C_{12}H_{24}O$): Calculated (%): C 78.20, H 13.12. Found (%): C 77.92, H 13.01.

IR analysis (thin film, cm$^{-1}$): 3650, 3550 ($\nu_{OH}$); 2950, 2920, 2860 ($\nu_{CH}$).

$^1$H-NMR (CDCl$_3$ solvent, TMS internal standard, δ): 2.03–1.35 [—(CH$_2$)$_4$—, 8H, m]; 1.20 (—OH, 1H, s);

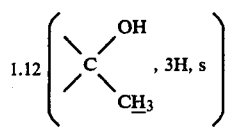

1.00 and 0.98 (—C$\underline{H}_3$, 12H, s).

MS (relative intensity): The results of a gas mass measurement using the same capillary column as used in Example 1 are shown below. 184(M+, 2), 99(33), 95(22), 86(27), 83(16), 82(100), 69(20), 55(20), 43(25), 41(16).

EXAMPLE 5

Synthesis of 1-ethyl-2,2,7,7-tetramethylcycloheptan-1-ol:

A mixed solution of ethyl bromide (33.30 g, 0.40 moles)/dried diethyl ether (40 ml) was dropped into a mixture of lithium (4.30 g, 0.62 moles)/dried diethyl ether (25 ml) in 2 hours while stirring at −30° C., followed by further adding dried diethyl ether (40 ml) and raising the temperature to 0° C. The mixture was subjected to separation by filtration. The resulting filtrate was dropped into a mixed solution of 2,2,7,7-tetramethylcycloheptanone (15.00 g, 0.09 moles)/dried diethyl ether (40 ml) in 30 minutes while stirring at 0° C. The mixture was stirred at 0° C. for 2 hours. The resulting reaction mixture was treated in the same manner as in Example 1 to obtain 13.50 g (yield 76.4%) of the captioned compound. This compound was a colorless transparent liquid having a woody, earthy and patchuli oil-like odor.

Boiling point: 108° C./5 mmHg.

Elementary analysis (for $C_{13}H_{26}O$): Calculated (%): C 78.72, H 13.21. Found (%): C 78.40, H 13.32.

IR analysis (liquid film, cm$^{-1}$): 3650, 3600 ($\nu_{OH}$); 2950, 2920, 2860 ($\nu_{CH}$).

$^1$H-NMR (CDCl$_3$ solvent, TMS internal standard, δ): 2.00–1.38 (—C$\underline{H}_2$—, 10H, m); 1.26 (—O$\underline{H}$, 1H, s); 1.15–0.77 (—C$\underline{H}_3$, 15H, m).

MS (relative intensity): The results of a gas mass measurement using the same capillary column as used in Example 1 are shown below. 198(M+, 0.4), 113(42), 100(92), 95(49), 85(28), 82(100), 69(45), 55(42), 43(31), 41(27).

EXAMPLE 6

Synthesis of 1-n-propyl-2,2,7,7-tetramethylcycloheptan-1-ol

1-Allyl-2,2,7,7-tetramethylcycloheptan-1-ol (15.00 g, 0.09 moles), 5 wt % Pd/C (1.00g, 0.33 wt % Pd) and n-hexane (20 ml) were added to an autoclave. The air in the autoclave was replaced by nitrogen, followed by applying to a H$_2$ pressure of 50 atm and heating the autoclave to 50° C. under stirring. The reaction was determined as completed at the time when the gas absorption was stopped. It required about 2 hours in this case. The autoclave was cooled down to room temperature and returned to a normal pressure, after which the content was withdrawn. The content was concentrated and subjected to fractionation to obtain 11.90 g (yield 77.6%) of the captioned compound. This compound was a colorless transparent liquid having a woody, earthy and patchuli oil-like odor.

Boiling point: 117° C./5 mmHg.

Elementary analysis (for $C_{14}H_{28}O$): Calculated (%): C 79.18, H 13.29. Found (%): C 78.85, H 13.11.

IR analysis (liquid film, cm$^{-1}$): 3650, 3600 ($\nu_{OH}$); 2960, 2920, 2860 ($\nu_{CH}$).

$^1$H-NMR (CDCl$_3$ solvent, TMS internal standard, δ): 2.05–1.43 (—C$\underline{H}_2$—, 12H, m); 1.32 (—O$\underline{H}$, 1H, s); 1.13–0.80 (—C$\underline{H}_3$, 15H, m). MS (relative intensity): The results of a gas mass measurement using the same capillary column as used in Example 1 are shown below. 212(M+, 0.5), 127(41), 114(82), 95(50), 82(100), 71(47), 69(47), 55(37), 43(41), 41(29).

EXAMPLE 7

Synthesis of 1-n-butyl-2,2,7,7-tetramethylcycloheptan-1-ol

A n-butyl lithium/n-hexane solution having a concentration of 1.6 moles/liter (70 ml, 0.11 moles of n-BuLi) was added, in 30 minutes, to a mixed solution of 2,2,7,7-tetramethylcycloheptanone (16.80 g, 0.10 mole)/dried diethyl ether (100 ml) while stirring at −5° C. The mixture was stirred at −5° C. for 1 hour. Subsequently, the reaction mixture was treated in the same manner as in Example 1 to obtain 16.00 g (yield 70.7%) of the captioned compound. This compound was a colorless transparent liquid having a woody, earthy and green odor.

Boiling point: 128° C./4 mmHg.

Elementary analysis (for $C_{15}H_{30}O$): Calculated (%): C 79.58, H 13.36. Found (%): C 79.63, H 13.28.

IR analysis (liquid film, cm$^{-1}$): 3650, 3600 ($\nu_{OH}$); 2960, 2920, 2860 ($\nu_{CH}$).

$^1$H-NMR (CDCl$_3$ solvent, TMS internal standard, δ): 2.05–1.42 (—C$\underline{H}_2$—, 14H, m); 1.32 (—O$\underline{H}$, 1H, s); 1.20–0.80 , (—C$\underline{H}_3$, 15H, m).

MS (relative intensity): The results of a gas mass measurement using the same capillary column as used in Example 1 are shown below. 226(M+, 0.4), 141(37), 128(67), 95(49), 85(39), 82 (100), 69(49), 57(46), 55(34), 41(30).

EXAMPLE 8

Fougere-type Perfume

|  | parts by weight |
|---|---|
| Lavender oil | 100 |
| Bergamot oil | 135 |
| Lavandine oil | 110 |
| Geranium oil | 30 |
| Coumarin | 30 |
| Geraniol | 100 |
| Citronellol | 100 |
| Geranyl acetate | 20 |
| Linalool | 40 |
| Oak moss absolute | 40 |
| Alpha-hexylcinnamic aldehyde | 40 |
| Sandal wood oil | 20 |
| Vetiver oil | 20 |
| Rose oil | 20 |
| Jasmine absolute | 5 |
| Amyl salicylate | 60 |
| Vetiveryl acetate | 50 |
| Musk ketone | 20 |
|  | 940 |

To 940 parts by weight of the fougere-type perfume of the above formulation was added 60 parts by weight of 1-allyl-2,2,6,6-tetramethylcyclohexan-1-ol, thereby obtaining a new fougere-type perfume felt sweet and dry.

EXAMPLE 9

Rose-type Perfume

|  | parts by weight |
|---|---|
| Geraniol | 150 |
| Citronellol | 200 |
| Geranium oil | 40 |
| Rose oxide 1% DPG* | 20 |
| Benzyl acetate | 10 |
| Phenylethyl acetate | 550 |
| Geranyl acetate | 10 |
| Eugenol | 10 |
| Nonyl aldehyde | 1 |
| Nonyl alcohol 10% DPG* | 1 |
| Phenyl acetoaldehyde | 1 |
|  | 993 |

*DPG: dipropylene glycol (diluent)

To 993 parts by weight of the above rose-type perfume was added 7 parts by weight of 1-allyl-2,2,6,6-tetramethylcyclohexan1-ol, thereby obtaining a rose-type perfume which had a much increased woodiness of natural rose.

EXAMPLE 10

Perfume for Men's Cologne

|  | parts by weight |
|---|---|
| 1-Allyl-2,2,7,7-tetramethylcycloheptan-1-ol | 150 |
| Cedryl acetate | 150 |
| Acetyl cedrene | 150 |
| Vetiver oil | 10 |
| Clove oil | 20 |
| Tree moss absolute | 40 |
| Amber base | 30 |
| Castoreum absolute | 5 |
| Galaxolide 50[1] | 50 |
| Celestolide[2] | 50 |
| Coumarin | 30 |
| Amyl salicylate | 20 |
| Jasmine absolute | 20 |
| Isobutylquinoline | 1 |
| Lavender oil | 50 |

-continued

|  | parts by weight |
|---|---|
| Undecylenic aldehyde | 2 |
| Ligstral[3] | 3 |
| Galbanum oil | 2 |
| Laurel oil | 40 |
| Gamma undecalactone | 1 |
| Nutmeg oil | 10 |
| Pine oil | 30 |
| Dipropylene glycol | 96 |
|  | 850 |

[1]Galaxolide 50: 1,3,4,6,7,8-hexahydro-4,6,6,7,8,8-hexamethylcyclopenta-gamma-2-benzopyran
[2]Celestolide: 4-acetyl-6-tert-butyl-1,1-dimethylindane
[3]Ligstral: 3,5(or 2,4)-dimethyl-3-cyclohexen-2-carboaldehyde 1-Allyl-2,2,7,7-tetramethylcycloheptan-1-ol was added to the perfume for men's cologne, thereby imparting freshness, warmness and volume to the preparation.

What is claimed is:

1. A cycloalkan-1-ol derivative of the following formula (I)

$$\underset{(CH_2)_n}{\overset{HO \quad R}{\bigtimes}} \quad (I)$$

in which R represents a hydrogen atom, lower alkyl group or allyl group, and n is an integer of 3 or 4 provided that when n is 3, R is not a hydrogen atom or lower alkyl group.

2. A perfume composition comprising an effective amount of a cycloalkan-1-ol derivative of the following formula (I)

$$\underset{(CH_2)_n}{\overset{HO \quad R}{\bigtimes}} \quad (I)$$

in which R represents a hydrogen atom, lower alkyl group or allyl group, and n is an integer of 3 or 4 provided that when n is 3, R is not a hydrogen atom or lower alkyl group.

* * * * *